(12) United States Patent
Weber et al.

(10) Patent No.: US 8,367,855 B2
(45) Date of Patent: Feb. 5, 2013

(54) PROCESS FOR PREPARING SILYLORGANOAMINES

(75) Inventors: Christoph Weber, Wiesbaden (DE); Dorit Wolf, Oberursel (DE)

(73) Assignee: Evonik Degussa GmbH, Essen (DE)

( * ) Notice: Subject to any disclaimer, the term of this patent is extended or adjusted under 35 U.S.C. 154(b) by 20 days.

(21) Appl. No.: 13/025,132

(22) Filed: Feb. 10, 2011

(65) Prior Publication Data

US 2011/0201835 A1    Aug. 18, 2011

(30) Foreign Application Priority Data

Feb. 12, 2010    (EP) .................................... 10153458

(51) Int. Cl.
*C07F 7/04*    (2006.01)
(52) U.S. Cl. ........................................................ 556/413
(58) Field of Classification Search ................ None
See application file for complete search history.

(56) References Cited

U.S. PATENT DOCUMENTS 5,101,055 A *   3/1992   Dinh et al. ...................... 556/413
6,417,381 B1 *  7/2002   Gedon et al. ................... 556/413

FOREIGN PATENT DOCUMENTS

EP    0 531 948 B1    7/1996

OTHER PUBLICATIONS

European Search Report for EP 11 15 4212.2 dated May 20, 2011.

* cited by examiner

*Primary Examiner* — Sudhakar Katakam
(74) *Attorney, Agent, or Firm* — Law Office of: Michael A. Sanzo, LLC

(57) ABSTRACT

Process for preparing silylorganoamines, which process comprises the following steps:
(A) provision of silylorganoamines of the formula I: $[R^2_a(R^1O)_{3-a}SiR^3]_n NH_{3-n}$ in a reactor,
(B) reaction of the silylorganoamines of the formula I in the presence of particulate metallic noble metal at a temperature in the range from 100° C. to 300° C. to form silylorganoamine products of the formula II:

$[R^2_a(R^1O)_{3-a}SiR^3]_y NH_{3-y}$, where each radical $R^1$ and each radical $R^2$ is selected independently from the group consisting of alkyl, aryl, aralkyl and cycloalkyl radicals having fewer than 20 carbon atoms; $R^3$ is selected from the group consisting of divalent hydrocarbon radicals having fewer than 20 carbon atoms and a=0, 1, 2 or 3; n=1 or n=2 or n=1 and 2; and y=3.

21 Claims, No Drawings

PROCESS FOR PREPARING SILYLORGANOAMINES

CROSS REFERENCE TO RELATED APPLICATIONS

The present application claims priority to European Application EP 10153458.4 filed on Feb. 12, 2010.

FIELD OF THE INVENTION

The invention presented here relates to a process for preparing tertiary amines containing organosilyl groups. Amines containing organosilyl groups are also referred to as silylorganoamines.

BACKGROUND OF THE INVENTION

Tertiary amines containing organosilyl groups are particularly suitable as bonding agents for glass and other materials. These amines also have a wide range of uses for the treatment of fabrics and for personal care products.

A process for preparing silylorganoamines is likewise disclosed by EP 0 531 948 B1, which discloses a specific process for preparing secondary and tertiary amines containing organosilyl groups by contacting silylorganoamines with palladium monoxide as catalyst. Although the process leads to virtually quantitative conversion of the starting materials, the amines prepared by the process according to EP 0 531 948 B1 have to be subjected to a further work-up, e.g. a distillation, in order to obtain the desired purity and product concentration.

DESCRIPTION OF THE INVENTION

It is therefore an object of the present invention to provide a further process for preparing tertiary amines containing organosilyl groups, in which the disadvantages of the prior art are at least reduced and which achieves high yields and high purities in a single-stage synthesis without a further work-up by distillation.

This object is achieved by a process for preparing silylorganoamines, which process comprises the following steps:
(A) provision of silylorganoamines of the formula I:

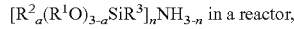 in a reactor, (B) reaction of the silylorganoamines of the formula I in the presence of particulate metallic noble metal at a temperature in the range from 100° C. to 300° C. to form silylorganoamine products of the formula II:

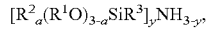

where each radical $R^1$ and each radical $R^2$ is selected independently from the group consisting of alkyl, aryl, aralkyl and cycloalkyl radicals having fewer than 20 carbon atoms; $R^3$ is selected from the group consisting of divalent hydrocarbon radicals having fewer than 20 carbon atoms and a=0, 1, 2 or 3; n=1 or n=2 or n=1 and 2 (i.e. a mixture of primary and secondary silylorganoamines); and y=3.

The process of the invention gives only tertiary amines containing organosilyl groups, i.e. the index "y" in formula II is 3.

The reaction preferably proceeds without use of solvents. The difficulty associated with use of a solvent is the high reaction temperature at which only a high-boiling solvent could be used. However, such a solvent would make a complicated work-up necessary.

In the process of the invention, metallic noble metal catalysts and base metal oxides as described, for example, in EP 0 531 948 B1 are used as catalyst. For the purposes of the present invention, noble metals are the elements of groups 8 to 10 of the 5th and 6th periods of the Periodic Table of the Elements.

For the purposes of the present invention, organosilyl groups of the silylorganoamines are substituents which have direct silicon-carbon bonds (Si—C). Such substituents are denoted by $R^2$ in the above formulae I and II. The silylorganoamines described by formulae I and II can contain from 0 to 3 substituents $R^2$.

However, for the purposes of the present invention, organosilyl groups of the silylorganoamines also include substituents in which the carbon is linked to the silicon via oxygen atoms, known as organooxy substituents. Such substituents are denoted by $R^1$ in the above formulae I and II. The silylorganoamines described by formulae I and II can contain from 0 to 3 substituents R.

The organosilyl groups can contain both substituents, but preference is given in the process of the invention to the organosilyl groups containing only substituents in which the carbon is linked via oxygen atoms to the silicon, i.e. index "a" in formula I and formula II is 0.

The silylorganoamines described by formulae I and II contain the substituent $R^3$ selected from the group consisting of divalent hydrocarbon radicals having fewer than 20 carbon atoms. $R^2$ can be, for example, an alkanediyl radical, a cycloalkanediyl radical, an arenediyl radical or a divalent radical of an aralkane.

Preferred amines described by formula I are those in which $R^1$ is a methyl, ethyl or phenyl radical; $R^2$ is a methyl or ethyl radical and $R^3$ is an alkanediyl radical having from 1 to 3 carbon atoms. The amine described by formula I can be, for example:
mono(trimethoxysilylpropyl)amine,
mono(vinyldimethoxysilylpropyl)amine,
mono(3,3,3-trifluoropropyldimethoxysilylpropyl)amine,
mono(methyldimethoxysilylpropyl)amine,
bis(trimethoxysilylpropyl)amine,
bis(methyl-dimethoxysilylpropyl)amine,
mono(triethoxysilylpropyl)amine,
bis(triethoxysilylpropyl)amine,
mono(phenyldimethoxysilylpropyl)amine,
bisphenyldimethoxysilylpropyl)amine and
mono(trimethoxysilylmethyl)amine
or mixtures of these substances.

The process described can be carried out in any standard reactor in order to effect contact between solids and liquids. The reactor can be, for example, a fixed-bed reactor, a reactor having a stirred bed or a fluidized-bed reactor.

The process of the invention enables the disadvantages of the prior art in respect of the required work-up by distillation to be overcome. High purities of the tertiary amine containing organosilyl groups can be obtained in a single-stage synthesis. Except for filtering off the catalyst, a further purification is unnecessary. A distillation or other purification processes can therefore be dispensed with.

Use of the process of the invention enables a primary silylorganoamine to be converted into a tertiary silylorganoamine. This is illustrated by way of example in the following reaction scheme under item I.

A secondary silylorganoamine can also be converted into a tertiary silylorganoamine (see reaction II in the following scheme) or a mixture of primary and secondary silylorganoamines can be converted into a tertiary silylorganoamine (see reaction III in the following scheme).

The possible reactions are shown by way of example for the preparation of tris(triethoxysilylpropylamine) in the following scheme.

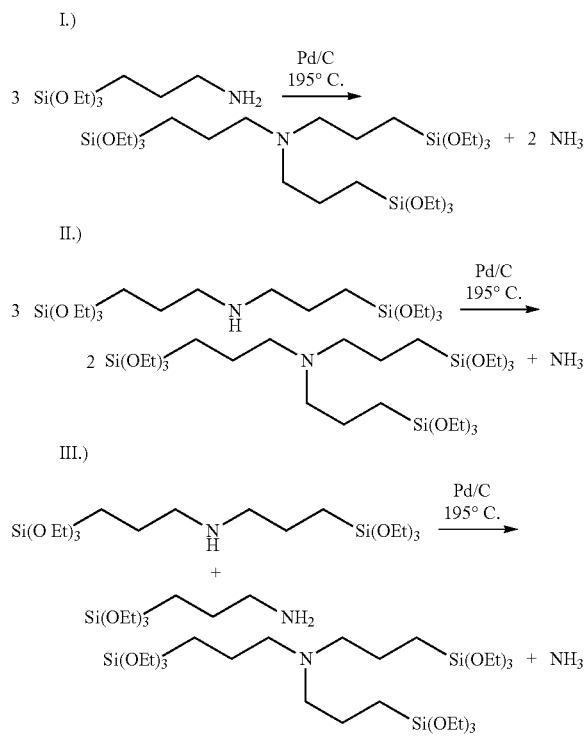

The catalyst component in the form of particulate metallic noble metal can contain small proportions of noble metal in oxidic or hydroxidic form. The proportion of metallic noble metal in the catalyst component should be not less than 20% by weight, and the proportion of metallic noble metal in the catalyst component is preferably at least 50% by weight, more preferably at least 75% by weight, particularly preferably at least 85% by weight, in particular at least 95% by weight.

The particulate metallic noble metal can be, for example, in the form of flocs, turnings, particles or powder. Preference is given to the particulate metallic noble metal being present in the form of particles or powder having an average particle diameter of less than 100 μm, particularly preferably less than 10 μm.

Preference is given to using palladium or rhodium as particulate metallic noble metal for the process of the invention.

The metallic noble metal is particularly preferably present on a support. As support, preference is given to using activated carbon or aluminium oxide.

Palladium on activated carbon as support is particularly preferably used as catalyst. The palladium component is metallic palladium which can contain small proportions of palladium in oxidic or hydroxidic form. The diameter of the palladium particles is typically 1 nm-20 nm, but preferably from 1.5 nm to 5 nm.

The activated carbon typically has a high porosity with proportions of macropores, mesopores and micropores. The pore volume is typically in the range 0.5-2.0 ml/g, preferably in the range 1.10-1.20 ml/g, the volume of micropores is 0.10-0.50 ml/g, preferably 0.30-0.40 ml/g and the mesopore volume is 0.10-1.00 ml/g, preferably 0.40-0.50 ml/g. The specific internal surface area (determined by the BET method) is typically in the range from 100 $m^2$/g to 2500 $m^2$/g, preferably from 200 $m^2$/g to 2000 $m^2$/g.

As an alternative, a rhodium catalyst supported on activated carbon can also be used, with the activated carbon support likewise having to meet the abovementioned requirements.

The noble metal concentration should advantageously be from 0.1 g to 2.0 g per mol of amine in the reactor. Preference is given to using a noble metal concentration of from 0.3 g to 0.6 g per mol of amine.

The process of the invention can be carried out in the presence of air. However, since, for example, palladium reacts in air to form palladium oxide and the catalytic activity can be reduced as a result, the reaction should, when the reaction takes place in an air atmosphere, be carried out under reduced pressure or in vacuo. Here, the pressure can be reduced down to 20 mbar. The reaction is preferably carried out in the range from 500 mbar to 900 mbar.

The reaction is preferably carried out in an inert gas atmosphere. For the purposes of the present invention, the term inert gas refers to nitrogen and all noble gases (helium, neon, argon, krypton, xenon, radon). In an inert gas atmosphere, the reaction can take place under atmospheric pressure, i.e. under ambient pressure.

The inert gas is preferably introduced continuously into the reactor during the reaction. The introduction can, if desired, also be carried out under the surface of the liquid reaction mixture, for example using a frit.

A low inert gas volume flow has the advantage that starting material is carried out only to a small extent, but this also applies to $NH_3$ which is formed as by-product. Although a high inert gas volume flow ensures good discharge of $NH_3$, too much starting material can be carried out at the same time. An inert gas volume flow of 1 ml-100 ml of inert gas per ml of reaction mixture and minute is usually set.

A further increase in the product yield is achieved by means of hydrogen as reactive gas. Preference is therefore given to hydrogen being introduced into the reactor during the reaction and a significant increase in the yield of tertiary amine compared to a reaction in the absence of hydrogen being achieved thereby. The hydrogen is particularly preferably introduced below the surface of the liquid reaction mixture. The hydrogen concentration can be from 0.1 to 99.999% by volume. Preference is given to a hydrogen concentration of from 1 to 3.8% by volume. Although hydrogen can be added even when the reaction space contains air, this is done only when the reaction is carried out below the lower explosive limit for hydrogen/oxygen mixtures. For this reason, hydrogen is preferably introduced as reactive gas when the reaction proceeds in an inert gas atmosphere.

The reaction is carried out at atmospheric pressure using inert gas or hydrogen or an inert gas/hydrogen mixture and leads to no precipitation of ammonia salts. The ammonia formed in the reaction is removed by the inert gas or the hydrogen or the $H_2/N_2$ gas mixture.

Examples of silylorganoamine products which can be prepared by the present process are:
tris(vinyldimethoxysilylpropyl)amine,
tris(3,3,3-trifluoropropyldimethoxysilylpropyl)amine,
tris(trimethoxysilylpropyl)amine,
tris(methyldimethoxysilylpropyl)amine,
tris(triethoxysilylpropyl)amine,
tris(phenyldimethoxysilylpropyl)amine,
tris(trimethoxysilylmethyl)amine.

The resulting product of the process of the invention is very particularly preferably tris(triethoxysilylpropyl)amine. Tris (triethoxysilylpropyl)amine serves as surface modifier or as building block for polyaminosiloxanes (organosiloxanamine copolymers).

Virtually quantitative conversion with high product purity is achieved in the process of the invention, so that further work-up of the product can be dispensed with. Yields of at least 70%, preferably at least 75% or at least 80%, particularly preferably at least 85%, are achieved.

The reaction time is dependent on the reaction temperature, the noble metal catalyst concentration and the desired product and can be in the range from 30 minutes to 20 hours. Preference is given to a reaction time in the range from 6 hours to 13 hours.

The reaction can be carried out in the range from 100° C. to 300° C., with preference being given to from 150° C. to 210° C.

EXAMPLES

The invention is illustrated with the aid of the following examples. The examples are for illustrative purposes and are not to be construed as a restriction.

Experimental Description CW88 (Palladium/Hydrogen)

596 mg of Pd/C catalyst (Degussa E 105 R/W 5%) and 21.0 g of bis(triethoxysilylpropyl)amine were placed in a 100 ml four-neck flask fitted with reflux condenser.

The mixture was firstly stirred at room temperature under argon (40 ml/min) for 15 minutes. A mixture of N2 (95% by volume) and H2 (5% by volume) was then introduced (120 ml/min), the mixture was stirred for a further 5 minutes and heated to a reaction temperature of 195° C.

After the temperature of >185° C. had been reached, samples were taken through a septum and analysed by gas chromatography.

The batch was turned off after about 6 h and on the next day heated to about 195° C. again for a further reaction time of about 6.

TABLE 1

Starting material and product concentration as a function of time for experiment CW88

| Reaction time [min] | Aminosilane [%] (GC) | Bisamino- silane [%] (GC) | Trisamino- silane [%] (GC) | others [%] (GC) |
|---|---|---|---|---|
| 60 | 1.6 | 20.7 | 72.3 | 3.4 |
| 120 | 1.4 | 14.6 | 78.5 | 3.8 |
| 240 | 0.8 | 9.9 | 82.2 | 5.4 |
| 360 | 0.7 | 8.9 | 84.5 | 4.7 |
| 760 | 0.1 | 5.9 | 87.7 | 6.3 |

Experimental Description CW92 (Palladium/Inert Gas):

596 mg of Pd/C catalyst (Degussa E 105 R/W 5%) and 21.0 g of bis(triethoxysilylpropyl)amine were placed in a 100 ml four-neck flask fitted with a reflux condenser. The mixture was firstly stirred at RT under argon (40 ml/min) for 15 minutes. Nitrogen (120 ml/min) was then introduced and the mixture was heated to about 195° C.

After the temperature of >185° C. had been reached, samples were taken through a septum and analysed by gas chromatography.

The batch was turned off after about 6 h and on the next day heated to about 195° C. again for a further reaction time of about 6.

TABLE 2

Starting material and product concentration as a function of time for experiment CW92

| Reaction time [min] | Aminosilane [%] (GC) | Bisamino- silane [%] (GC) | Trisamino- silane [%] (GC) | others [%] (GC) |
|---|---|---|---|---|
| 60 | 3.2 | 26.6 | 61.8 | 8.5 |
| 120 | 2.5 | 16.3 | 70.9 | 10.3 |
| 240 | 2.8 | 10.8 | 74.8 | 11.6 |
| 360 | 2.1 | 9.1 | 77.2 | 11.6 |
| 760 | 2.4 | 6.0 | 79.8 | 11.8 |

TABLE 3

Results for the preparation of tris(triethoxysilyl-propyl)amine (*tris) using a supported Pd/C noble metal catalyst

| Exp | Cat | Starting material | CC | Pr | Tmp | Gas type | RT | CT1 | CT2 |
|---|---|---|---|---|---|---|---|---|---|
| CW88 | Pd/C | bis(triethoxy-silylpropyl)amine | 0.6 | atm | 195 | H2/N2/Ar | 760 | 91 | 87.7 |
| CW92 | Pd/C | bis(triethoxy-silylpropyl)amine | 0.6 | atm | 195 | N2/Ar | 760 | 83 | 79.8 |

Abbreviations used in Table 3

Exp = Experiment

Cat = Catalyst

CC = Catalyst concentration $g_{noble\ metal}/mol_{substrate}$

Pr = Pressure [mbar]

Tmp = Temperature [° C.]

RT = Reaction [min]

CT1 = Content$_{tris}$* mol[%] (NMR)

CT2 = Content$_{tris}$* [%] (GC)

What is claimed is:

1. A process for preparing tertiary silylorganoamines, comprising reacting silylorganoamines of formula I:

$$[R^2_a(R^1O)_{3-a}SiR^3]_n NH_{3-n} \text{ (I)}$$

in a reactor, in the presence of a particulate metallic noble metal catalyst, wherein the proportion of metallic noble metal in said catalyst is at least 50% by weight, at a temperature in the range of from 100° C. to 300° C. to form silylorganoamine products of the formula II:

$$[R^2_a(R^1O)_{3-a}SiR^3]_y NH_{3-y} \text{ (II)}$$

wherein:
each radical $R^1$ and each radical $R^2$ is independently selected from the group consisting of: alkyl, aryl, aralkyl and cycloalkyl radicals having fewer than 20 carbon atoms;
$R^3$ is selected from the group consisting of: divalent hydrocarbon radicals having fewer than 20 carbon atoms; and
a = 0, 1, 2 or 3;
n = 1 or 2,
and y = 3.

2. The process of claim 1, wherein the reaction is performed using a mixture of silylorganoamines in which n = 1 and n = 2.

3. The process of claim 1, wherein a = 0.

4. The process of claim 1, wherein said metallic noble metal is palladium or rhodium.

5. The process of claim 1, wherein said metallic noble metal is present on a support.

6. The process of claim 1, wherein the reaction is carried out under an inert gas atmosphere.

7. The process of claim 6, wherein said inert gas is introduced continuously into the reactor during the reaction.

8. The process of claim 6, wherein hydrogen is introduced into the reactor during the reaction.

9. The process of claim 7, wherein the gases are introduced under the surface of a liquid reaction mixture.

10. The process of claim 3, wherein said metallic noble metal is palladium or rhodium and wherein the proportion of metallic noble metal in said catalyst is at least 75% by weight.

11. The process of claim 10, wherein said metallic noble metal is present on a support.

12. The process of claim 10, wherein the reaction is carried out under an inert gas atmosphere.

13. The process of claim 12, wherein said inert gas is introduced continuously into the reactor during the reaction.

14. The process of claim 13, wherein hydrogen is introduced into the reactor during the reaction.

15. The process of claim 14, wherein the gases are introduced under the surface of a liquid reaction mixture.

16. The process of claim 1, wherein:
$R^1$ is a methyl, ethyl or phenyl radical;
$R^2$ is a methyl or ethyl radical; and
$R^3$ is an alkanediyl radical having from 1 to 3 carbon atoms.

17. The process of claim 16, wherein a = 0.

18. The process of claim 17, wherein said metallic noble metal is palladium or rhodium and wherein the proportion of metallic noble metal in said catalyst is at least 75% by weight.

19. The process of claim 18, wherein said metallic noble metal is present on a support.

20. The process of claim 19, wherein the reaction is carried out under an inert gas atmosphere.

21. The process of claim 1, wherein the proportion of metallic noble metal in said catalyst is at least 95% by weight.

* * * * *